(12) United States Patent
Faraldi et al.

(10) Patent No.: US 9,939,390 B2
(45) Date of Patent: Apr. 10, 2018

(54) METHOD FOR DETECTING DEFECTS IN A ROD-SHAPED TRANSPARENT OBJECT

(71) Applicant: Prysmian S.p.A., Milan (MI) (IT)

(72) Inventors: Antonio Faraldi, Milan (IT); Gerardo Testa, Milan (IT); Antonio Adigrat, Milan (IT); Franco Cocchini, Milan (IT)

(73) Assignee: PRYSMIAN S.P.A., Milan (IT)

( * ) Notice: Subject to any disclaimer, the term of this patent is extended or adjusted under 35 U.S.C. 154(b) by 0 days.

(21) Appl. No.: 14/899,840

(22) PCT Filed: Jun. 25, 2013

(86) PCT No.: PCT/EP2013/063271
§ 371 (c)(1),
(2) Date: Dec. 18, 2015

(87) PCT Pub. No.: WO2014/206450
PCT Pub. Date: Dec. 31, 2014

(65) Prior Publication Data
US 2016/0139062 A1 May 19, 2016

(51) Int. Cl.
*C03B 37/025* (2006.01)
*G01N 21/954* (2006.01)
(Continued)

(52) U.S. Cl.
CPC ......... *G01N 21/954* (2013.01); *C03B 37/025* (2013.01); *G01M 11/088* (2013.01);
(Continued)

(58) Field of Classification Search
None
See application file for complete search history.

(56) References Cited

U.S. PATENT DOCUMENTS

| 2006/0115913 A1* | 6/2006 | Orita ................ C03B 37/01446 438/22 |
| 2008/0192239 A1 | 8/2008 | Otosaka |

(Continued)

FOREIGN PATENT DOCUMENTS

| CN | 1340155 A | 3/2002 |
| CN | 1934432 A | 3/2007 |

(Continued)

OTHER PUBLICATIONS

JP10167744A Google Patents Machine Translation performed Nov. 14, 2016.*

(Continued)

*Primary Examiner* — Lisa L Herring
(74) *Attorney, Agent, or Firm* — Shumaker, Loop & Kendrick, LLP

(57) ABSTRACT

A method for inspecting defects inside a rod-shaped transparent object by using a scanning beam of parallel light rays directed onto a rod-shaped transparent object orthogonally to the longitudinal axis of the object so that an inspection plane comprises an object's cross-section. The scanning beam is detected at an opposite side of the rod-shaped object that is interposed to intercept the parallel rays of the scanning beam. The electric output signal from the detector is processed to produce a first light intensity profile in a first scan direction, the light intensity profile comprising a shadow region delimited by first and second shadow edges, which is indicative of the outside diameter of the object across the inspection plane. The method comprises analyzing the first light intensity profile to determine the presence or absence of a peak of positive intensity within the shadow region and, if an intensity peak is determined to be present, to determine the presence or absence of a region of depressed intensity within the intensity peak. If, as a result of analyzing, an intensity peak within the shadow region is determined to be absent or a region of depressed intensity is determined to be present within the intensity peak, the (Continued)

presence of at least one structural defect within the object's cross-section is identified. In the preferred embodiments, the rod-shaped transparent object is a glass core rod for the production of a transmission optical fiber.

11 Claims, 9 Drawing Sheets

(51) Int. Cl.
    *G01M 11/00*    (2006.01)
    *G01M 11/08*    (2006.01)

(52) U.S. Cl.
    CPC ..... *G01M 11/37* (2013.01); *G01N 2021/9548* (2013.01); *G01N 2201/06113* (2013.01); *G01N 2201/105* (2013.01)

(56) References Cited

U.S. PATENT DOCUMENTS

2011/0132037 A1* 6/2011 Ishida ................ C03B 37/0253
                                                                 65/378

2011/0157582 A1* 6/2011 Cocchini ............. C03B 37/0253
                                                                 356/73.1

FOREIGN PATENT DOCUMENTS

| EP | 0256539 A2 | 2/1988 |
| JP | 10-167744 A | 6/1998 |
| JP | 10167744 A * | 6/1998 |
| JP | 2010-139441 A | 6/2010 |

OTHER PUBLICATIONS

European Patent Office Search Report for PCT/EP2013/063271 dated Mar. 14, 2014.
Liu W et al: Joint Transform Correlator for the Detection of Defects in Optical Fibers, Optical Engineering, Soc. of Photo-Optical Instrumentation Engineers, Bellingham, vol. 37, No. 5, May 1, 1998 pp. 1468-1473, XP000777072, ISSN: 0091-3286, DOI: 10.1117/1.601662.
Office Action for Chinese Patent Appln. No. 201380077774.8, dated Sep. 13, 2017 (14 pages including English translation).

* cited by examiner

METHOD FOR DETECTING DEFECTS IN A ROD-SHAPED TRANSPARENT OBJECT

FIELD OF THE INVENTION

The present invention relates to a method for inspecting structural defects inside a rod-shaped transparent object. In particular, the invention concerns a method for inspecting structural defects, such as bubbles, voids or inclusions, in a glass core rod for optical fibres, in particular for transmission optical fibres. The present invention also relates to a process of elongating a glass preform for the production of an optical fibre, in particular a transmission optical fibre.

BACKGROUND OF THE INVENTION

Optical fibre technology requires characterization and control of various fibre properties during the process of manufacturing of the fibre from a preform.

Fibre performance in general depends on the geometric uniformity and the dimensions of the core and cladding layers of the optical fibre. The outer diameter is generally measured at a point shortly after the fibre is formed during the drawing process, typically immediately below the neck-down region.

U.S. Pat. No. 4,280,827 describes a fibre diameter measurement circuit including a source, a detector that senses the presence of interference fringes, wherein the detector signal is connected to two signal comparing means via a respective delay circuit connected to the source. The outputs from the signal comparing means are combined and counted in order to generate a succession of counts representative of the diameter of successive axial portions of the advancing fibre.

To obtain high-quality fibres, structural defects, such as holes or bubbles, should be minimised or avoided. Holes or bubbles typically occur at the centre of the fibre, although they can be located anywhere in the fibre cross-section.

U.S. Pat. No. 5,185,636 describes a method and an apparatus for detecting defects in optical fibres based on different parameters from those used to measure fibre diameter so that the steps of diameter control and defect detection can be uncoupled in the overall detection system. The disclosed techniques are based on effects on the far-field interference pattern produced by holes.

In U.S. Pat. No. 6,313,909 a scattered light signal is filtered and the resulting signal is compared to a defect detection threshold to determine the presence of defect-related components in the scattered light signal.

U.S. Pat. No. 5,406,374 describes a method for inspecting a rod-like optical fiber preform for the presence of bubbles and/or inclusions comprising photographing images scattered by the bubbles/inclusions through a side face of the preform by a video camera while light rays are incident upon the whole end face of the preform from a white lamp and discriminating and detecting the bubbles/inclusions through image-analysis of image signals of the photographed images. Light rays are incident upon the optical fiber preform and photograph of the images of the preform by the video camera are made while rotating the optical fiber preform around the longitudinal axis of the optical fiber preform.

A synthetic quartz drawing apparatus provided with a detector for bubbles is disclosed in JP 10167744 A.

A testing device is disclosed in WO 2011/052541, having a detector detecting the forward scattering light intensity distribution of a preform, while rotating the preform by a rotating mechanism. A determination unit determines from the light intensity distribution whether through-holes are formed at predetermined positions.

Various technologies for optical fiber production may lead to the formation of holes or bubbles trapped in the fibre. For example, core preforms formed by Outside Vapor Deposition (OVD) are obtained by deposition of silica and doped silica soot on a target. At the end of the deposition process, the target is removed resulting in a soot preform with a central hole. The soot preform is consolidated and then stretched so that the central hole is collapsed thereby forming a glass core rod having a surface region with low or no dopant content.

In a known process, described in US 2003/0140658, after creating a vacuum in the central hole, the consolidated core preform is placed in a vertical furnace in which the fusion of a lower end of the preform is carried out. The fusion of the lower end causes the walls of the hole to collapse because of the vacuum created in the hole. The fused glass material cools, forming an elongated cylindrical element of a predetermined diameter, which is stretched downwards by a traction device. The disclosed apparatus for applying traction to an elongated element is provided with an opto-electronic sensor placed in the proximity of the upper portion of the elongated cylindrical element for measuring the diameter.

The collapse of the hole during stretching can be incomplete and/or take place with the generation of defects. Core preforms made by Modified Chemical Vapour Deposition (MCVD), by Plasma Chemical Vapour Deposition (PCVD) processes or by other inside vapour deposition processes may exhibit a similar problem.

A final glass preform to be drawn into an optical fibre can be produced by depositing cladding glass soot onto the core rod, for example by an OVD process, followed by consolidation.

Optical micrometers for determining the position and the dimension of an object of circular cross-section are known.

U.S. Pat. No. 4,492,473 discloses an opto-electronic measuring device utilising a rotating mirror to produce a scanning beam which is then collimated, directed at an object to be measured, and the light then collected and a digital pulse train derived therefrom representing the position of the object, by utilizing a shaft encoder which is driven by the same motor which rotates the mirror for the generation of pulse signals which are proportional to the angular velocity of the encoder and the mirror.

U.S. Pat. No. 4,991,308 concerns a diameter gauge for measuring the outside diameter of a part having a circular cross-section. The gauge comprises two arms converging to form a V-shaped channel, a light source positioned along one side of the channel and, opposite the light source, along the other side of the channel, a light detecting device.

In U.S. Pat. No. 5,175,595, a non-contact measuring device is described, in which light generated from a source of light that is allowed to enter a polygonal mirror rotating at a constant speed via a lens. The light that is reflected by the polygonal mirror is then allowed to enter a collimator lens to thereby turn the light into a scanning light movable in parallel to the optical axis of the collimator lens and to allow the light to be focused at the position of an object to be measured.

U.S. Pat. No. 6,278,520 relates to an optical micrometer for measuring the maximum diameter of work pieces, e.g. a tapered cutting tool, along the length of the work piece. A laser micrometer for measuring a work piece, which includes: means for generating a laser beam path such that a portion of said beam path passes by a part of the work piece; means for receiving and processing said portion of said beam path to determine size of said first part; a V-shaped seat having a first side surface and a second side surface, wherein said surface form a seat to receive the work piece, and wherein the V-shaped seat seats the work piece to permit at least a portion of the work piece to be disposed within said beam path; and apparatus for rotating said work piece to cause slidable rotation of said work piece in said V-shaped seat such that said work piece is maintained in contact with said two sides while seated therein by said apparatus.

SUMMARY OF THE INVENTION

Defects positioned in the central region of the optical fibre, namely the core region where most of the light signal is guided, and the inner cladding region next adjacent to the core region where tails of the light signals extend, are very likely to cause the degradation of optical performances. For this reason, consolidation and/or elongation processes represent critical stages of the overall manufacturing process of an optical fibre.

The Applicant has observed that identification of holes or bubbles during drawing of an optical fibre from a preform, while making possible to achieve fibre quality, may be inefficient due to the fact that an end product, when defective, is discarded as waste.

The Applicant has further noted that methods of inspection of an optical fibre preform using photographs of a side face of the preform by a video camera, such as the method described in U.S. Pat. No. 5,406,374, may suffer from the limitation that effectiveness strongly depends on the quality of the optical devices (e.g. CCD camera and/or lenses) and on the cleanness of the surface of the preforms to be tested.

Apparatuses for elongating (i.e. stretching) glass core preforms are commonly equipped with an optoelectronic device for the measurement of the outside diameter of the elongated preform, wherein the diameter is measured downstream the neck down. The diameter measurement is generally used as a feedback for traction speed control and/or for monitoring other process parameters.

A device that can be employed for the measurement of the outside diameter of the elongated core preform uses the general principles of the micrometer of U.S. Pat. No. 6,278, 520, namely a parallel light beam irradiates the elongated preform at the exit of the furnace and a detector detects the shadow cast by the preform, thereby providing a measurement of the diameter in the inspected cross-section.

The Applicant has noticed that, in case of glass preforms, due to the transparency of the glass, the shadow is due not to the irradiated object blocking the transmission of the light beam (as in case of opaque objects), but it is mainly due to a strong deflection of the incident beam. This principle is schematically illustrated in FIG. 1, showing a cross-sectional view of a rod-shaped transparent object irradiated by a parallel scanning beam. In FIG. 1, a transparent object 1 of circular cross-section having refractive index n>1 deviates some of the parallel rays 2 to oblique directions. The diameter of object 1 is determined by the shadow, which extends in a cross-sectional plane of the object in a direction perpendicular to the incident scanning beam. The actual measurement of the object's outside diameter is unaffected by the deflection of the incident rays, since the shadow on a detection plane remains the same, as it will be more detailed in the following. Transmitted rays (deflected and uninterrupted) are focused by a lens system, exemplified in the figure by a converging lens 7, onto a photodetector 35. The photodetector collecting the transmitted rays has a finite size that determines a detected scanned region, represented in the figure with arrow 8. Due to the detector's finite size, there exists a maximum angle at which light can be collected, which is herein indicated as maximum angle of acceptance, $\theta_{max}$. As a first approximation, the maximum angle depends on the size of the photodetector and on the main optical parameters of the focusing lens system, for example focal length(s) and refraction index of the lenses.

A distance d, indicated in FIG. 1 with reference number 5, is defined as the distance from the central axis 6 of the beam passing through the axial centre C of object 1 along the direction of the incident rays. A light ray 2 incident on the object at a distance d is deflected at a deflection angle. If the distance d is larger than a given minimum distance, $d_{min}$, light ray 2 emerges as deflected ray 4 with a deflection angle $\theta$ that is larger than $\theta_{max}$, and thus the light ray is not collected by the photodetector, as schematically indicated by ray 34 exiting the lens system.

The photodetector 35 is configured to detect a scanned region 8, in a scan direction (indicated in the figure with an arrow) perpendicular to the incident direction, in a cross-sectional plane of the object. The scanned region is larger than the cross-section of the object to be measured. The shadow ranges approximately from tangential ray 9 to tangential ray 9' corresponding to the shadow edges on the detection plane, e.g. in which the detecting surface of the photodetector is placed.

The Applicant has observed that, if $d \leq d_{min}$, the deflection angle is such that the ray illuminates a central part of the shadow. FIG. 2 is a schematic representation of this condition. Same items of FIGS. 1 and 2 are indicated with same reference numbers. Light ray 31 impinges on object 1 at a distance $d \leq d_{min}$ from central axis 6 and is deflected by a deflection angle $\gamma \leq \theta_{max}$, i.e. small enough to fall onto the detector. Transmitted rays are focused by a lens system, exemplified in the figure by a converging lens 7, onto photodetector 35. In particular, deflected ray 33 is focused into ray 37 that is collected by the photodetector. Dotted area 32 graphically represents the area of the cross-section of the rod-shaped object, across which incident rays are deflected by an angle equal to or smaller than the maximum acceptance angle $\theta_{max}$ of the receiving detector.

The Applicant has realized that the illuminated portion of the shadow region is affected by the presence of structural defects in the analysed object. Therefore, it is possible to reliably detect defects, such as bubbles or voids, across a glass core rod for the production of an optical fibre. In particular, it is possible to detect defects in an axially central region of the rod, where defects are expected to mostly affect the optical performances of the end product.

According to some preferred embodiments, disclosed method is cost-effective since it allows the on-line monitoring of defects at an early stage of the manufacturing process of an optical fibre. In some preferred embodiments, monitoring can be carried out by means of a device which is often used on an apparatus for stretching core preforms for the control of the outside diameter of the stretched preform.

According to an aspect consistent with the present disclosure, a method for inspecting defects inside a rod-shaped transparent object is provided, the method comprising:
  generating a first scanning beam of parallel light rays sweeping an inspection plane in a first scan direction;
  directing the first scanning beam onto a rod-shaped transparent object having a longitudinal axis and being arranged in such a way that the inspection plane is transverse to the longitudinal axis of the object and comprises an object's cross-section;

detecting the first scanning light beam at an opposite side of the rod-shaped object that is interposed to intercept the parallel rays of the scanning beam, thereby producing a first electric output signal;

processing the first electric output signal to produce a first light intensity profile in the first scan direction, the light intensity profile comprising a shadow region delimited by first and second shadow edges, the width between the first and second shadow edges being indicative of the outside diameter of the object across the inspection plane;

analysing the first light intensity profile to determine the presence or absence of a peak of positive intensity within the shadow region, the peak originating from deflected rays transmitted through the object and detected, and, if an intensity peak is determined to be present, to determine the presence or absence of a region of depressed intensity within the intensity peak.

If, as a result of analysing, an intensity peak within the shadow region is determined to be absent or a region of depressed intensity is determined to be present within the intensity peak, the method further comprises identifying the presence of at least one structural defect within the object's cross-section.

Preferably, identifying the presence of at least one structural defect comprises activating an alarm.

In an embodiment, activating an alarm comprises:

recording a longitudinal position of the object's cross-section along the longitudinal axis at which either the absence of the peak or the presence of a depressed region is positively determined as defective cross-section.

Preferably, after recording the longitudinal position of the defective cross-section, the method comprises retrieving the longitudinal position and discarding a longitudinal section of the rod-shaped object comprising the defective cross-section.

According to some preferred embodiments, the first intensity profile has a scan maximum value originating from the scanning beam transmitted uninterrupted without interposition of the object, and analysing the light intensity profile comprises:

setting a threshold intensity value smaller than the scan maximum intensity value, and determining if a plurality of intensity values of the first intensity profile exceed the intensity threshold value across the shadow region between the first and second shadow edges for checking the presence or absence of an intensity peak within the shadow region;

if the intensity of the first intensity profile is determined to be smaller than the threshold value across the shadow region, an intensity peak is determined to be absent;

if a plurality of intensity values exceed the threshold value across the shadow region, an intensity peak is determined to be present and analysing further comprises determining if the intensity peak has a region of intensity values smaller than the intensity threshold value for checking the presence or absence of a region of depressed intensity, and if a region of intensity values smaller than the threshold value is determined to be present within the intensity peak, a region of depressed intensity is determined to be present.

Preferably, the intensity threshold value is selected within the range of from 20% to 80% of the scan maximum intensity value, more preferably, of from 30% to 70% of the scan maximum intensity value.

Preferably, the inspection plane is orthogonal to the longitudinal axis of the rod-shaped object.

Preferably, the first scanning beam of parallel light rays is of monochromatic light.

Preferably, generating a first parallel scanning light beam comprises:

generating a light beam of monochromatic light;

directing the light beam onto a rotating mirror to produce a scanning light beam in an inspection plane, and collimating the scanning beam to produce a parallel scanning beam of parallel light rays in the inspection plane to be directed onto the rod-shaped transparent object.

In the preferred embodiments, the rod-shaped transparent object is a glass core rod for the production of an optical fibre.

The intensity peak is delimited in the first scan direction by first and second peak edges and has a peak maximum intensity value. In some embodiments, across the depressed intensity region, intensity values are significantly smaller than the peak maximum value, namely at least 20% smaller than the peak maximum value.

The depressed region within the intensity peak is delimited in the first scan direction by a first and second depression edges defining a width of the depressed region. Preferably, the method further comprises:

determining the width of the depressed region, retrieving a correlation function between width values and diameters of structural defects as a calibration curve, and calculating the diameter of the at least one detected structural defect by using the correlation function.

According to some embodiments, the depressed region is located at a central region within the intensity peak.

In an embodiment, analysing comprises:

setting a threshold intensity value smaller than the scan maximum intensity value;

determining the number of times the light intensity profile crosses the threshold intensity value in the first scan direction, and determining from the number of crossings the presence or absence of a peak of positive intensity within the shadow region and, if an intensity peak is determined to be present, the presence or absence of a depressed region within the intensity peak.

In an embodiment, the light intensity profile ranges from an initial scan edge to a final scan edge in the scan direction and determining from the number of crossings the presence or absence of an intensity peak or of a depressed region within the peak comprises:

if the number of crossings is two in the first scan direction, the intensity peak within the shadow region is determined to be absent, if the number of crossings is four in the first scan direction, the intensity peak is determined to be present and a depressed region within the intensity peak is determined to be absent, and if the number of crossings is six in the first scan direction, an intensity peak and a depressed region within the intensity peak are determined to be present.

If, as a result of analysing, the number of crossing if determined to be two or six, the presence of at least one structural defect within the object's cross-section is identified.

According to some preferred embodiments consistent with the present disclosure, a method for inspecting defects inside a rod-shaped transparent object is provided, the method comprising:
  generating a first scanning beam of parallel light rays sweeping an inspection plane in a first scan direction;
  generating a second scanning beam of parallel light rays sweeping a plane in a second scan direction;
  directing the first scanning beam onto a rod-shaped transparent object having a longitudinal axis and being arranged in such a way that the inspection plane is transverse to the longitudinal axis of the object and comprises an object's cross-section;
  directing the second scanning beam onto the rod-shaped transparent object in such a way that the plane swept by the second scanning beam corresponds to the inspection plane and first and second scanning beams of parallel rays cross one another orthogonally in an area of the inspection plane that comprises an object's cross-section in the inspection plane, the second scan direction being orthogonal to the first scan direction;
  detecting the first and second scanning light beam at a respective opposite side of the rod-shaped object that is interposed to intercept the parallel rays of the respective first and second scanning beam, thereby producing a respective first and second electric output signals;
  processing the first and second electric output signals to produce, respectively, a first intensity profile in the first scan direction and a second intensity profile in the second scan direction, each of the first and second light intensity profiles comprising a shadow region delimited by first and second shadow edges, the width between the first and second shadow edges being indicative of the outside diameter of the object across the inspection plane;
  analysing the first and second light intensity profiles to determine, for each profile, the presence or absence of a peak of positive intensity within the shadow region and, if an intensity peak is determined to be present, to determine the presence or absence of a region of depressed intensity within the intensity peak for each profile;
  comparing the first intensity profile with the second intensity profile to determine if (a) an intensity peak is absent in both first and intensity profiles, or (b) an intensity peak within the shadow region is present in both first and second intensity profiles and a region of depressed intensity is present in both first and second intensity profiles, or (c) an intensity peak is determined to be absent in one of first and second scan profiles and an intensity peak with a depressed region is determined to be present in the other of first and second scan profiles, and
  if, as a result of comparing, one of the conditions (a) to (c) is satisfied, identifying the presence of at least one centrally located structural defect in the inspected object's cross-section.

Without wishing to be bound by explanation, condition (c) indicates a centrally located structural defect that is very large in one axial direction and smaller in the other axial direction, thus lacking axial symmetry.

Preferably, identifying at least one centrally located structural defect comprises activating an alarm. Preferably, activating an alarm comprises recording a longitudinal position of the object's cross-section along the longitudinal axis as defective cross-section, the longitudinal position being the position at which (1) either the absence of the peak or the presence of a depressed region is positively determined in both first and second scan profiles or (2) a positive intensity peak is determined to be absent in one of first and second scan profiles and the intensity peak with a depressed region is determined to be present in the other of first and second scan profiles.

In some embodiments, the first intensity profile has a first scan maximum value and the second intensity profile has a second scan maximum value, the first and second scan maximum values originating from the respective first and second scanning beams transmitted uninterrupted without interposition of the object in the respective scan direction, wherein:
  analysing the first light intensity profile comprises setting a first threshold intensity value smaller than the first scan maximum value and determining a first number of times the first light intensity profile crosses the first threshold intensity value in the first scan direction;
  analysing the second light intensity profile comprises setting a second threshold intensity value smaller than the second scan maximum value and determining a second number of times the second light intensity profile crosses the second threshold intensity value in the second scan direction;
  comparing comprises comparing the first number of crossings with the second number of crossings to determine if the first and second numbers are equal one another, and, if first and second numbers of crossings are equal one another, determining if the value of first and second numbers is two or six, and, if the first number is not equal to the second number, determining if the first number of crossings is equal to two and the second number is equal to six, and
  if, as a result of determining, either first and second numbers are equal one another and have a value of two or six or the combination of first and second numbers is two and six, identifying the presence of at least one centrally located structural defect in the object's cross-section.

Preferably, the first and second threshold values are equal one another in relation with the respective scan maximum intensity. Preferably, first and second threshold values are set to a value of from 20% to 80% of the respective first and second scan maximum value, more preferably of from 30% to 70%.

According to some preferred embodiments, the rod-shaped transparent object is a glass core rod for the manufacturing of an optical fibre and the method is carried out in combination with a process for elongating a glass core preform comprising:
  providing a glass core preform;
  heating the glass core preform within a furnace so as to soften a lower portion thereof, and
  submitting the glass core preform to a traction which comprises pulling the softened lower end of the core preform out of the furnace along an advancement direction so as to form a glass core rod as a rod-shaped transparent object,
  wherein directing the first scanning beam of parallel light rays is directing the first scanning beam onto the glass core rod, the inspection plane is positioned downstream the furnace along the advancement direction, and the glass core rod moves in the advancement direction, vertically relative to the inspection plane.

Preferably, submitting a traction is carried out while rotating the glass core rod about its longitudinal axis.

Preferably, the glass core rod rotates uniformly at a rotation speed of from 4 to 8 rpm.

Preferably, the longitudinal axis of the glass core rod is along the advancement direction.

Preferably, the glass core rod moves in the advancement direction at an advancement speed of from 15 to 25 cm/min.

Preferably, detecting the first scanning beam is performed at a first angular position of the rotating glass core rod and the method further comprises repeating detecting the first scanning beam at a second angular position of the rotating glass core rod during a single rotation to produce an additional electric output signal, processing the additional electric output signal into an additional light intensity profile in the first scan direction, analysing the additional light intensity profile, and identifying the presence of at least one structural defect within the object's cross-section at the second angular position if, as a result of analysing the additional intensity profile, an intensity peak within the shadow region is determined to be absent or, if an intensity peak is determined to be present, a region of depressed intensity determined to be present within the intensity peak.

According to an aspect consistent with the present disclosure, a process for elongating a glass preform for the production of an optical fibre is provided, the process comprising:
  providing a glass core preform;
  heating a glass core preform within a furnace so as to soften a lower portion thereof, and
  submitting the preform to a traction which comprises pulling the softened lower end of the core preform out of the furnace along an advancement direction so as to form a glass core rod, and
  inspecting the glass core rod for defects in an inspection plane downstream the furnace,
  wherein inspecting is carried out according to the method in accordance with the main features of the present disclosure.

Preferably, the glass core rod is for the manufacturing of an optical fibre preform to be drawn into a single-mode optical fibre for optical communication systems.

In some embodiments, inspection of a core rod, and more generally of a rod-shaped transparent object, is carried-out off-line, for example by vertically moving the object with respect to the inspection plane.

BRIEF DESCRIPTION OF THE DRAWINGS

The present invention will now be described in more detail hereinafter with reference to the accompanying drawings, in which some, but not all embodiments of the invention are shown. Drawings illustrating the embodiments are not-to-scale schematic representations.

For the purpose of the present description and of the appended claims, except where otherwise indicated, all numbers expressing amounts, quantities, percentages, and so forth, are to be understood as being modified in all instances by the term "about". Also, all ranges include the maximum and minimum points disclosed and include any intermediate ranges therein, which may or may not be specifically enumerated herein.

FIG. 7b is a graph schematically reproducing the intensity profile of FIG. 7a.

DETAILED DESCRIPTION

Figure 3:
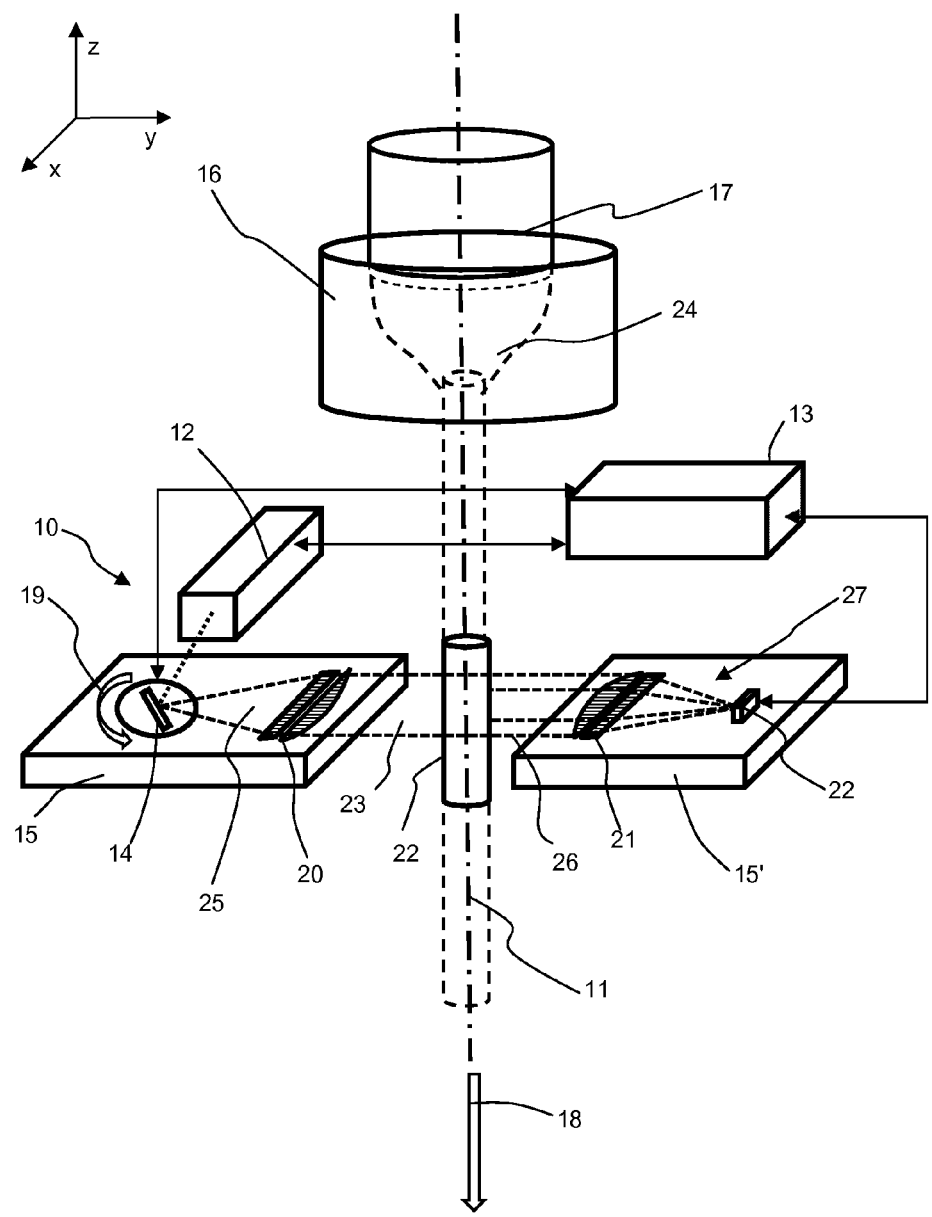
FIG. 3 is a schematic representation of an apparatus to implement a method in accordance with an embodiment consistent with the present disclosure.

FIG. 3 is a diagrammatic perspective view of an inspection apparatus in combination with a stretching apparatus for the elongation of a glass core preform, in accordance with an embodiment consistent with the present disclosure. In the embodiment, an inspection apparatus 10 for inspecting a glass elongated object 22 is provided. The elongated object has a generally cylindrical shape and extends along a longitudinal axis 11 (z axis). According to the preferred embodiments, the inspection apparatus 10 is used for on-line monitoring during elongation (stretching) of a glass core preform. A glass core preform 17 is fed vertically into a furnace 16, in a per se known manner. The glass core preform is made of silica, doped with suitable dopants (selected according to the optical transmission properties to be obtained), at least in an axially central region to form a core region for guiding the light. Doped inner cladding region(s) next adjacent to the core region may be present for engineering the confinement of the light in the core. Typical diameters of core preforms can range approximately from 50 mm to 100 mm. The furnace is capable of housing the core preform coaxially with the vertical axis of advancing direction of the preform.

Figure 1:
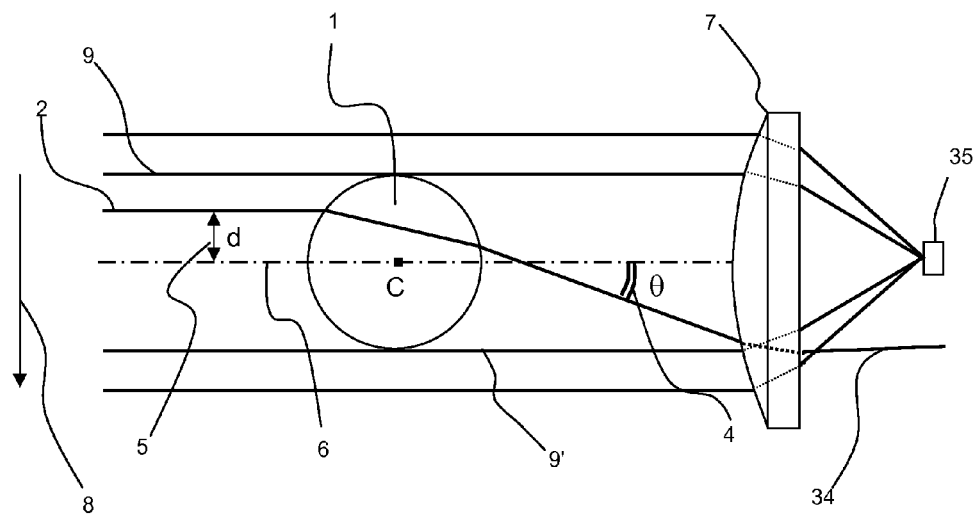
FIG. 1 is a schematic diagram showing the path of transmitted rays by a transparent object shown in a cross-sectional view.

Within the furnace, the lower end portion 24 of the preform 17 is heated up to the glass softening temperature, e.g. 1,800-1,900° C., forming a "neck down" due to gravity and to the pulling force exerted by a traction device connected to a lower end of the preform. The melted portion flows out the furnace 16 and cools while being stretched downwards so as to form an elongated core preform 22 of specific diameter, in the following referred to as core rod. The pulling force is indicated in FIG. 1 by arrow 18, whereas the traction device is not shown in the figure. Traction device is per se known. For example, a traction apparatus of the type described in US 2003/0140658 can be employed. Preferably, the advancing direction of the core rod is along the longitudinal axis 11 of the core rod.

In some embodiments, the glass core preform is produced from dehydration and consolidation of a soot core preform, for example made by an OVD process, and has a central hole. Melting of the lower end portion of the glass core preform causes the collapse of the walls of the central hole and thus the closing of the hole. In a manner per se known, collapse is facilitated by applying a vacuum to the central hole. In other embodiments, the glass core preform is produced by an inside deposition technique in which glass layers are deposited on the inner diameter of a substrate tube by methods known as PCVD, MCVD or variants thereof. Subsequent traversing a heat source over the substrate tube with inner deposited glass layers causes collapse of the tube into a solid glass core preform.

Traction force is selected so as to produce a core rod with typical diameter ranging from 10 mm to 30 mm. Core rods of typical length of 1 to 2 meters are severed from the continuous rod exiting the traction device. Preferably, the core rod has a core region of doped-silica glass surrounded by an inner cladding region of substantially undoped silica.

The inspection apparatus 10 is positioned external from the furnace 16 and downstream the neck down 24 with respect to the advancing direction, i.e. z axis. In this way, an advancing vertical section of the core rod can be inspected for the presence of structural defects, such as bubbles, voids or inclusions.

The inspection apparatus 10 comprises an optical source 12 configured to emit a coherent light beam, preferably in the visible spectrum, directed to a rotatable scanner 14, which produces a scanning beam 25 sweeping an area on a plane in which a collimating optical system 20 is arranged. The collimating optical system 20 produces a scanning beam 23 of parallel light rays, in the following referred to as the parallel scanning beam. In an embodiment, the collimating optical system 20 comprises an optical edge sensor and one or more collimating lenses. The optical edge sensor is configured to sense the image edges and to provide the initial and final time of each beam sweep. The rotatable scanner and the collimating optical system are arranged so that the incident light beam 23 irradiates the core rod 22 in a direction transverse to its longitudinal axis 11, and preferably perpendicular to it, namely perpendicular to the advancing direction of the elongated object (y axis). In practice, the parallel rays of the incident scanning beam pass through a cross-section of the rod. The plane swept by the parallel scanning beam is referred to as the inspection plane. The parallel scanning beam sweeps the inspection plane (x,y) in a direction (x axis) perpendicular to the incident direction (y axis).

Preferably, the optical source 12 is a laser device. For example, the laser device is a low power HeNe laser emitting a collimated beam in the visible spectrum at 630 nm. Preferably, the rotatable scanner 14 is a rotatable mirror, which is configured to rotate at a constant angular rate $d\beta/dt$ across a scan angle $\beta$, indicated in FIG. 3 with bowed arrow 19, sufficiently wide so that the area swept by the reflected beam, i.e. the scanning beam, is larger than the cross section of the elongated object to be measured.

The beam transmitted through the core rod is collected by a receiving system 27 comprising a focussing optical system 21, e.g. a collection lens, operably arranged so as to receive the transmitted scanned beam, i.e. the uninterrupted rays and the rays deflected by the object, and a photodetector 22. The focussing optical system focuses the collected light onto the photodetector, which is operably arranged so as to receive the collected scanned light. Components 14 and 20 for producing a scanned incident beam and the receiving system 27 for collecting the scanned beam transmitted through the elongated object can be placed on a respective bench plates 15 and 15'. In the arrangement, the transparent object intercepts the parallel scanning beam and the receiving system is disposed at the opposite side of the object from the optical source, in position to receive the rays transmitted through the object.

The photodetector 22 preferably comprises edge sensing preamplifier electronics for detecting the start and end of each sweep and it is operably connected to a signal processor 13 configured to receive the output signal from the photodetector. Preferably, the signal processor is configured to control the operation of the laser device 12 and of the rotatable scanner 14 (control lines are indicated in the figure with double-pointed arrows). For example, the photodetector is a photodiode.

The processor can be connected to a display of a computer (not shown in FIG. 3) for the visualisation of the intensity profile.

In an embodiment, the signal output can be visualised by an oscilloscope (not shown in FIG. 3) connected to the photodetector output. In case analysis of the measurements is made using an oscilloscope, a camera picture can be taken of the oscilloscope screen, which can be further processed in a computer.

The signals output from the photodetector 22 are processed by the signal processor 13 to produce a light intensity profile of the detected scan. In particular, the intensity of the transmitted light measured in the forward direction for each angle step of the scan angle $\beta$ forms an intensity profile, which can be represented as a function of time, once the angular rate, $d\beta/dt$, of the rotating mirror during a scan is known. Thus, a scan period T corresponds to the scan angle $\beta$.

The inspection apparatus can be a commercial equipment, such as an apparatus AccuScan LD1025-S by Beta Laser-Mike, which is employed for the measurement of the outside diameter of elongated objects.

Figure 4:
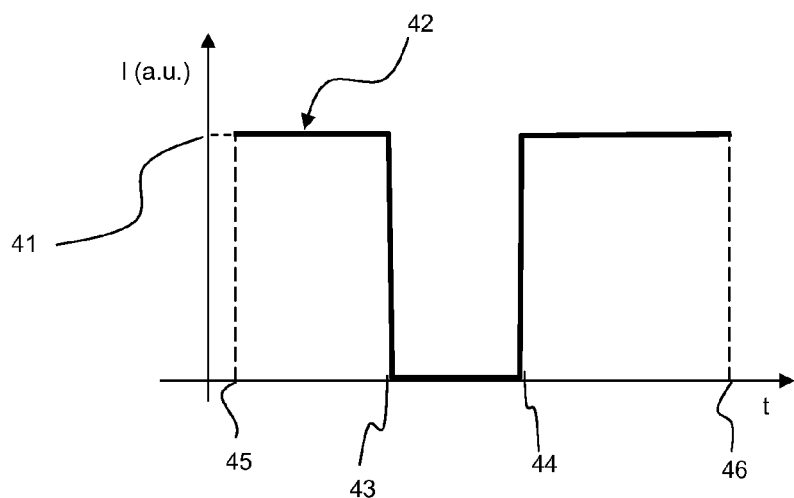
FIG. 4 is a schematic graph showing a typical intensity profile vs. time of a scan for an opaque cylindrical object.

FIG. 4 is a graph reporting a typical intensity profile of a scan with the intensity (ordinate) of the detected beam versus time (abscissa) obtained when an opaque cylindrical object is disposed in the measuring window of the inspection apparatus, i.e. in the inspection plane. For explanation purposes, line 42 representing the intensity profile is schematically drawn and, for example, does not reproduce experimental noise.

In an embodiment, the intensity profile of the graph can result from a measured intensity profile processed by a smoothing mathematical function, per se known.

In FIG. 4, the abscissa represents the time axis. The scan starts at time 45, i.e. initial scan edge, and ends at time 46, i.e. final scan edge. The intensity of the signal 42 remains at a maximum value 41 outside the time interval between points 43 and 44, where the signal drops to zero because of the shadow cast behind the opaque object. Points 43 and 44 are referred to as shadow time edges. The maximum value of the intensity originates from uninterrupted transmitted scanning beam impinging on the photodetector.

In the present description and claims with scan maximum intensity of a scan it is meant the intensity value of the scan beam detected without interposition of an object, namely representing the uninterrupted parallel scanning beam.

The shadow time edges 43 and 44 correspond to two respective angular positions of the rotating mirror of the inspection apparatus of FIG. 3. By knowing the angular rate of the rotation of the mirror during the scan, it is possible to determine the outside diameter of the opaque object from the measurement of the time interval between the shadow time edges. For example, for the analysis of elongated objects having an outside diameter of from 15 mm to 17 mm, the time interval between the shadow edges is of about 300 μs, the value depending inter alia on the angular rate of the mirror during the scan.

Figure 5:
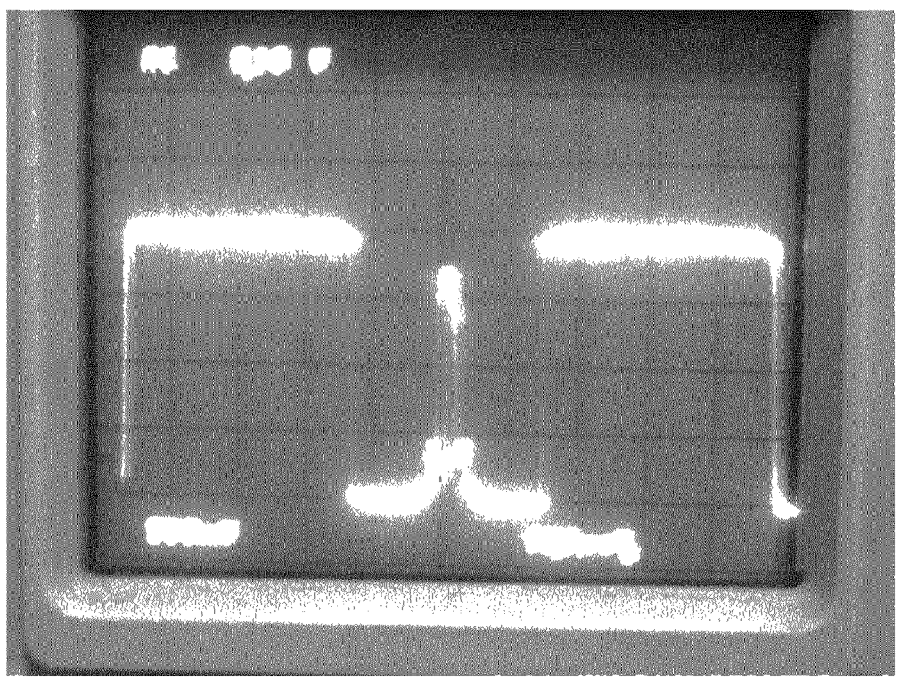
FIG. 5 is a snapshot of a camera picture of an oscilloscope screen showing an experimental intensity profile (white line) vs. time for a rod-shaped transparent object.

FIG. 5 is a snapshot of a camera picture of an oscilloscope screen showing an experimental intensity profile (analog trace shown as a white line) of a scan in the scan direction, which was measured by an inspection apparatus of the type described with reference to FIG. 3 for a glass core rod for the manufacturing of an optical fibre preform.

Figure 2:
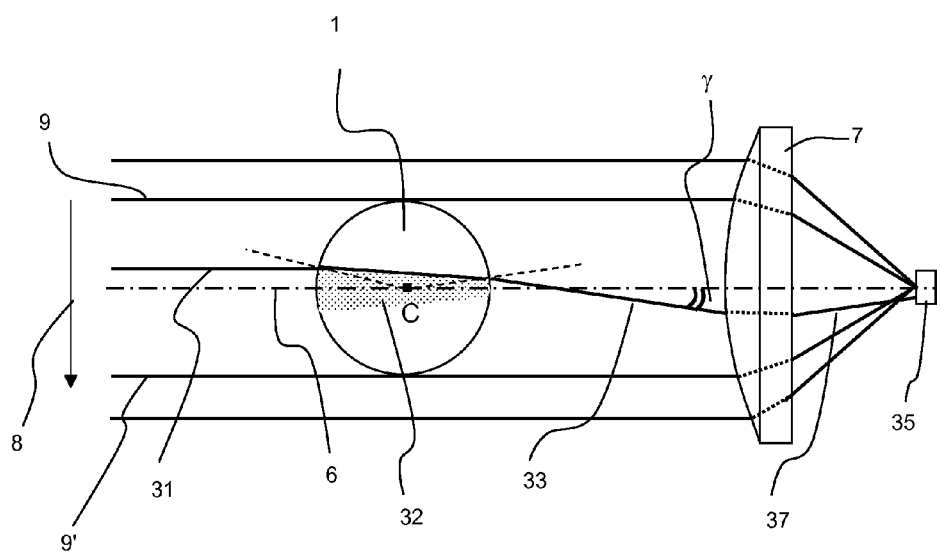
FIG. 2 is a schematic diagram showing the path of transmitted rays by a transparent object shown in a cross-sectional view.
Figure 6:
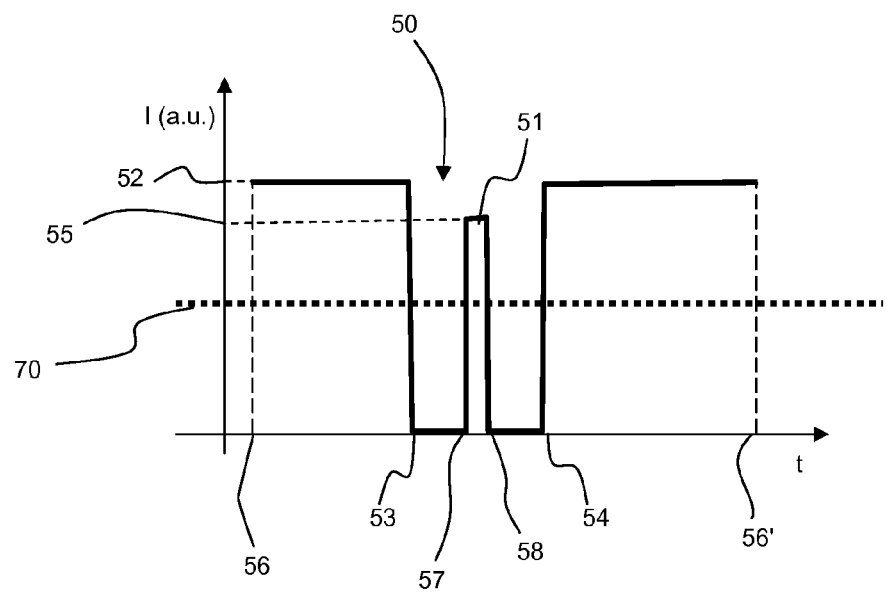
FIG. 6 is a graph of the intensity profile schematically representing the experimental data of FIG. 5.

FIG. 6 is a graph schematically representing the experimental intensity profile of FIG. 5, for purpose of clarity and for ease of discussion. The intensity profile 50 vs. time (t) ranges from an initial scan edge at time 56 to a final scan edge at time 56' and exhibits first and second shadow edge at times 53, 54 corresponding to two respective angular positions of the rotating mirror, in which tangential rays 9 and 9' of FIGS. 1 and 2 are collected. The outside diameter of the core rod can thus be determined from the extent of the shadow region between the shadow edges 53 and 54.

The intensity profile of FIG. 6 exhibits an intensity peak 51 in the middle of the shadow region, where the signal raises up to a relatively large intensity value 55, albeit typically slightly lower than the scan maximum intensity value 52. The intensity peak 51 ranges from first peak edge at time 57 to second peak edge at time 58.

Without wishing to be bound by theory or to a particular explanation, the intensity peak within the shadow region originates from the rays incident on the transparent object at a distance $d \leq d_{min}$ from the axis parallel to the rays and passing through the centre of the object's cross-section, as described with reference to FIG. 2. Under this condition, incident rays are deflected by passing through the object by an angle small enough to allow the deflected rays to be focused on the photodetector. As previously described, the ability of detecting rays deflected by an angle γ not larger than a given value, $\theta_{max}$, mainly depends on the size of the photodetector and on the focusing optical system in front of the photodetector.

Figure 7A:
FIG. 7a shows an enlarged section of the experimental intensity profile of FIG. 5.
Figure 7B:
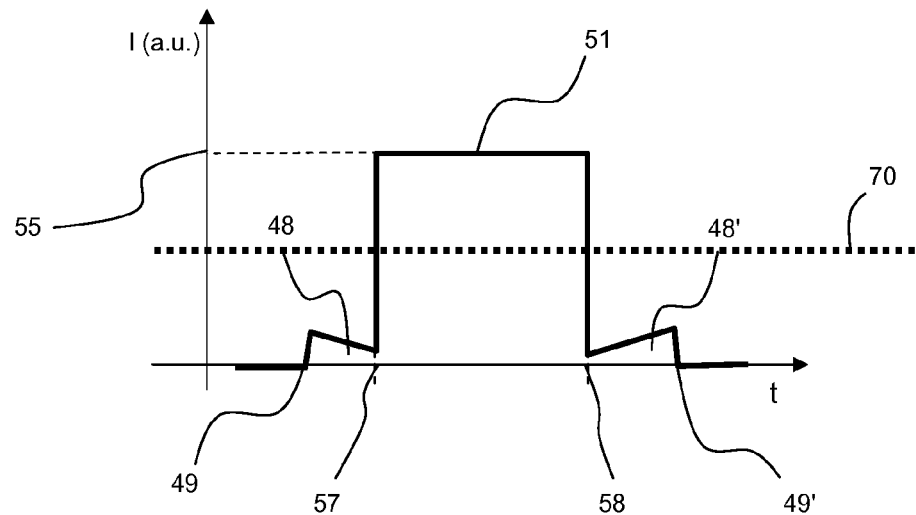

FIG. 7a is a snapshot of a camera picture of an oscilloscope screen showing the experimental intensity profile of FIG. 5, on an enlarged scale centred at the positive intensity peaks within the shadow area. FIG. 7b is a graph schematically reproducing the intensity profile of FIG. 7a. Within the shadow area, the intensity profile exhibits a positive intensity inner region 51 having a central peak that can be assumed of nearly constant intensity value 51 (disregarding experimental fluctuations, see FIG. 7a) between peak edges 57 and 58. The maximum peak value 51 was generally observed to be smaller than the scan maximum value 70, typically ranging between 85% and 95% of the scan maximum intensity value.

The positive intensity region exhibits two lateral "tails" 48, 48' of low intensity at the sides of the intensity peak extending from the peak edges to respective times 49 and 49'. Without wishing to be bound by theory or a particular explanation, it is believed that lateral tails in the intensity peak are due to the relatively large dip in the refractive index profile of the core rod analysed in the present example. A relatively large central dip in the refractive index profile of the core region is typical for core rods made by an OVD process. In fact, the Applicant observed that such lateral tails were in general not present for example in core rods made by PCVD or produced after chemical etching of the inner surface of the central part. The shape of the tails of the intensity peak provides therefore a first indication on the sensitivity of the signal to a perturbation of the very internal part of the rod (i.e. a relatively wide central dip of the refractive index profile of the core region). Were the lateral tails absent, edges of the positive inner region and peak edges would overlap.

In the following description and claims, with intensity peak within the shadow time interval it is meant the intensity peak extending between peak edges, i.e. disregarding possible low-intensity lateral tails, which are of considerably smaller intensity than the peak value, namely smaller than 30% of the largest intensity value of the peak and typically smaller than 10-20%.

Analysis of the intensity profile between scan times 57 and 58 provides information on the presence of structural defects in the analysed cross-section of the glass core rod. In the intensity profile of FIGS. 5, 6, 7a-7b no defects are detected, as the peak within the shadow region is present and has a nearly constant intensity value.

According to some preferred embodiments, analysis of the intensity profile comprises setting a threshold intensity value and determining if the intensity values across the intensity peak is smaller than the threshold value. The threshold value is indicated in FIGS. 6 and 7 with dotted line 70. If the result of the determination is in the negative (namely, no intensity values are determined to be smaller than the set threshold 70, no defects are identified in the inspected cross-section of the core rod.

Figure 8:
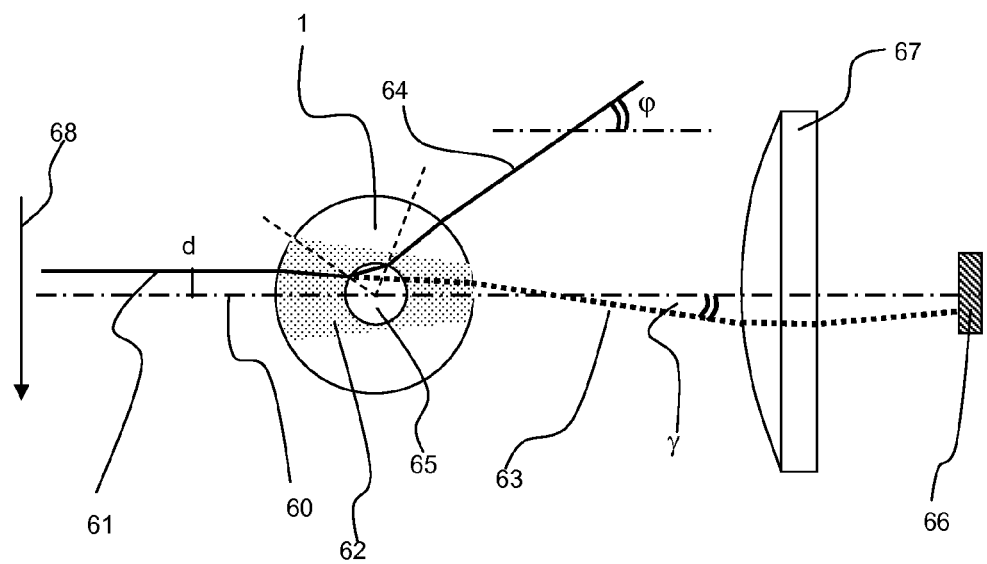
FIG. 8 is a schematic diagram showing the path of transmitted rays by a rod-shaped transparent object having a structural defect.

FIG. 8 is a schematic diagram showing the path of transmitted and deflected rays by a glass core rod (shown in a cross-sectional view) containing a defect in a central region of the cross-section. An incident scanning beam made of parallel light rays (scan time indicated with arrow 68) irradiates a glass core rod 1, which has a defect 65 located at the axial centre of the object. Incident ray 61 enters the object at a distance d from the central axis 60 passing through the axial centre C of object 1 along the direction of the incident rays. If distance d is not larger than $d_{min}$, ray 61 falls within the detectable cross-sectional area of the rod, indicated with dotted area 62. Were defect 65 not present, ray 61 would be transmitted through the object as ray 63 (dotted line), which would be deflected with respect to the direction of the incident beam by an angle γ lower than the maximum angle of acceptance of the receiving system. In this example, the receiving system comprises a photodetector 66 and a converging lens 67 that focuses ray 63 onto the photodetector. In absence of defects, deflected ray 63 would thus be collected by the photodetector, thereby contributing to the central intensity peak within the shadow area.

In the presence of a structural defect within the object, along the optical path of incident ray 61, the incident ray is scattered by the defect with a direction of scattered ray 64 forming a deflection angle φ much larger than angle γ, and in general larger than the maximum acceptance angle. Therefore, scattered ray 64 does not hit the photodetector and thus the intensity of the ray, which would be counted up to the central intensity peak, is "lost".

Defects to be detected by a method consistent with the present disclosure have a significant difference in refractive index with respect to the refractive index of the glass matrix of the core rod, condition generally satisfied by structural defects typically found in glass preforms made from common deposition techniques used for the manufacturing of optical fibre, namely voids and air or gas bubbles in a glass matrix.

Figure 9:
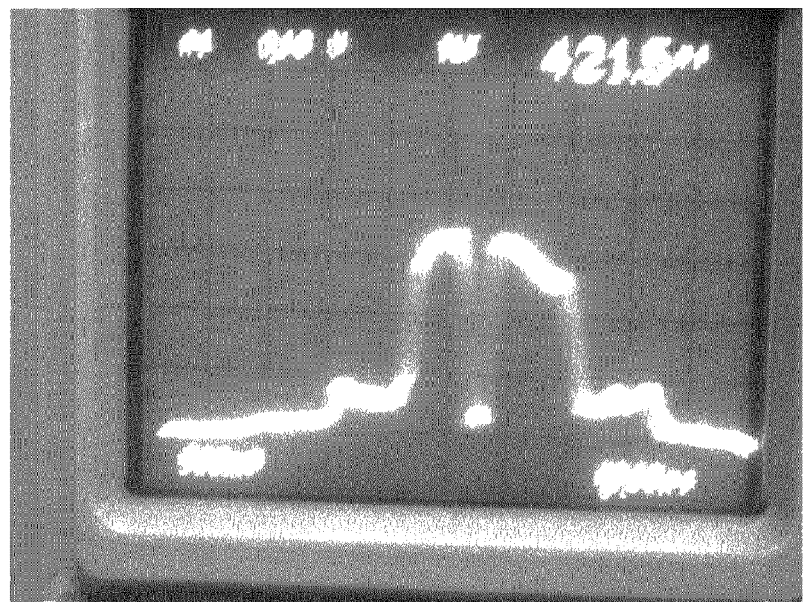
FIG. 9 is a snapshot of a camera picture of an oscilloscope screen showing the central portion of the experimental intensity profile (analog trace shown as a white line) of a scan resulting from a measurement.

FIG. 9 is a snapshot of a camera picture of an oscilloscope screen showing an experimental intensity profile (analog trace shown as a white line) of a scan measured by an inspection apparatus of the type described with reference to FIG. 3 for a core rod having a structural defect, for example arranged along the longitudinal axis of the rod. Only a central section of the scan on an enlarged scale, showing the intensity peak within the shadow area for a glass core rod, is visualized in the oscilloscope screen.

Figure 10:
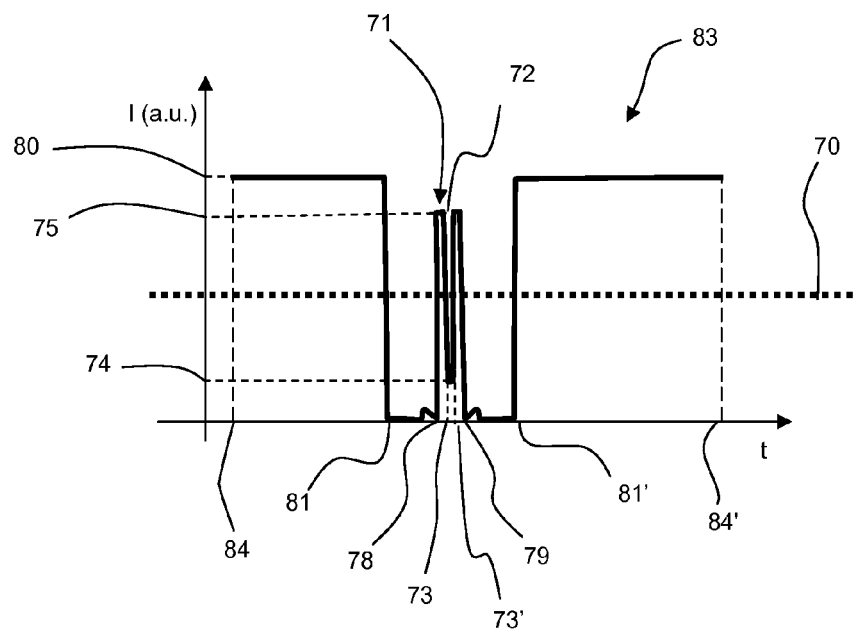
FIG. 10 is a schematic graph of the intensity profile schematically representing experimental data of FIG. 9, however reporting the entire intensity profile in the scan direction.
Figure 11:
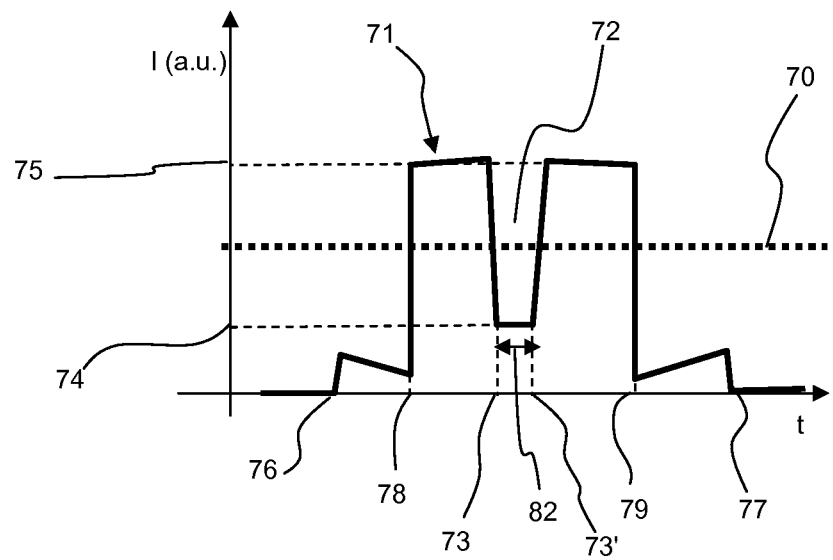
FIG. 11 is a graph derived from the experimental intensity profile of FIG. 9 reporting the intensity profile vs. time (i.e. central enlarged portion of FIG. 10).

FIG. 10 is a graph schematically representing the experimental intensity profile of FIG. 9, however reporting the entire intensity profile in the scan direction as a function of scan time. The central portion of the graph derived from the experimental intensity profile of FIG. 9 is shown in FIG. 11, on an enlarged scale with respect to FIG. 10. FIGS. 9 to 11 are exemplary intensity profiles representing the case of the detection of structural defects.

The intensity profile 83 vs. time (t) ranges from an initial scan edge at time 84 to a final scan edge at time 84' and exhibits a first and second shadow edge at times 81, 81', respectively. The outside diameter of the core rod can be determined from the extent of the shadow region between the shadow edges 81 and 81'. The intensity profile 83 has a scan maximum value 80 originating from uninterrupted transmitted scanning beam impinging on the photodetector.

The positive intensity inner region extends from times 76 to 77 and the intensity peak 71 extends between peak edges 78 and 79 (disregarding the lateral tails). It has been observed that intensity values at about the peak edges 78 and 79 are generally close to the maximum value 75 of intensity across the positive peak of the shadow region, said maximum peak value approximately corresponding to the intensity value of the peak of FIG. 7, originating from deflected rays entering the photodetector. The maximum peak value 75 was observed to be smaller than the scan maximum value 80, often ranging between 85% and 95% of the scan maximum value.

The intensity peak exhibits a region 72 of depressed intensity. The Applicant has understood that the presence of a depressed region within the central intensity peak is associated with the presence of a structural defect within the glass rod.

In FIG. 11, the depth of the depressed intensity region is indicated as the difference between the maximum intensity 75 of the peak and the intensity 74 across the depressed region. Across the depressed intensity region, intensity values are significantly smaller than the peak value, namely at least 20% smaller than the peak value.

Preferably, a depressed region within the light intensity peak identifies a structural defect within the inspected object if the depth of the depressed region across the depressed region is smaller than a threshold intensity value, which is set at a value smaller than the scan maximum intensity value of the intensity profile associated with the uninterrupted parallel scanning beam. In FIGS. 10 and 11, the threshold intensity value is indicated with dotted line 70.

Preferably, the intensity threshold value is of from 20% to 80% of the scan maximum value, more preferably of from 30% to 70% of the scan maximum value. In an embodiment, the threshold value is set at 50% of the scan maximum value so that values below 50% of the scan maximum value within the intensity peak identify the presence of a structural defect.

The scan maximum intensity value can be determined by analysing the experimental intensity profile (e.g. by means of a mathematical function that finds the maximum value in the scan direction) or it can be retrieved as a stored value associated with the experimental conditions at which the inspection apparatus has measured the intensity profile.

In some embodiments, the threshold value can be set with relation to the maximum value of in the intensity peak. In these embodiments, preferably, analyzing the intensity profile comprises determining the presence of absence of an intensity peak within the shadow area; in the positive, determining the maximum intensity value of the peak; setting a threshold intensity value smaller than the maximum intensity value of the peak, and determining if the intensity values across the intensity peak is smaller than the threshold value.

The method in accordance with some embodiments of the present disclosure allows an analysis of the defect size. In particular, the Applicant has understood that the width of the depressed region provides an indication of the diameter of the defect.

With reference to FIG. 11, the width 82 of the region of depressed intensity is defined between a first depression edge 73 and a second depression edge 73'. In the exemplary scan profile of the figure, the first depression edge is positioned at a larger time, in the scan direction, than the first peak edge 78 and the second depression edge is positioned at a smaller time than the second peak edge 79, namely the depressed region is internal the intensity peak and, in some cases of interest, centrally located within the peak.

A calibration curve for the determination of the size of the detected defects is built from the measurement of plurality of defects of known diameter by using an inspection apparatus according to the present disclosure.

Figure 12:
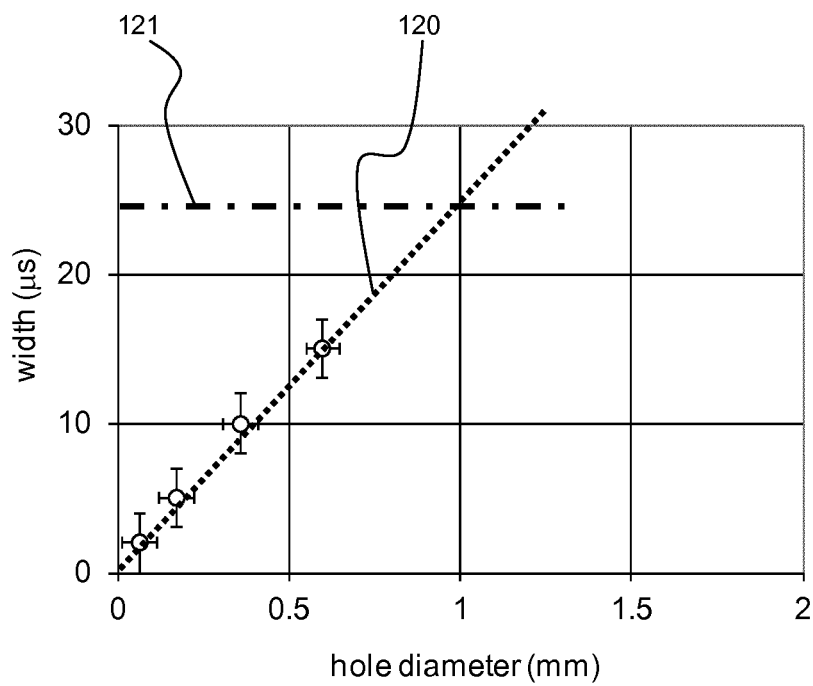
FIG. 12 is a plot showing a calibration curve of time width of the depressed region (μs) within the central intensity peak of a scan recorded at a respective defect of known diameter in glass core rods.

FIG. 12 is a plot showing the relationship between width of the depressed region (µs) within the central intensity peak of a scan recorded at a respective defect in glass core rods and the known diameter of the defect. The relationship width vs. diameter can be well approximated by a linear correlation, represented by dotted interpolation line 120. Results were obtained by measuring core rods of outside diameters of nearly 16 mm, corresponding to a shadow area (i.e. difference between time 54 and time 53 in FIG. 6) of 300 µs. Scans were detected by a photodiode having a finite size of diameter of about 5 mm. The width of the intensity peak within the shadow area (i.e. the difference between time 57 and time 58 in FIG. 7b) was nearly 25 µs, represented by dashed-dotted line 121 in FIG. 12. A scan time of 25 µs corresponds to a hole diameter of nearly 1 mm, which is therefore the maximum value of diameter which can be measured by the inspection apparatus of the present example. More generally, the Applicant noted that internal structural defects of diameter of from about 0.05 mm to 1 mm can be detected in glass core rods having a diameter up to about 25 mm.

Selection of a suitable receiving system of the inspection apparatus may take into account the dimension of the defects expected to be found in the glass preforms when it is desired to derive quantitative information from the measurement. For example, on a photodiode with relatively small collection surface (e.g. diameter size of less than about 5 mm), large holes (e.g. of at least about 1 mm) may cause the occurrence of depressed regions of depth as large as, or larger than the peak intensity originating from rays deflected from an homogenous core rod. This occurrence does not allow the determination of the defect dimension. However, it allows the determination of the presence of a hole or bubble, which is associated to the disappearance of the central bright zone. Namely, the partial or total disappearance of the central intensity peak provides an indication that a hole is present.

In the embodiments in which analysis of the intensity profile is performed using a threshold value, if intensity values within the shadow region are determined to be smaller than the threshold value, the presence of a structural defect is identified.

The light intensity profile in the scan direction is analysed, for example by processor 13, to determine if the intensity is smaller than a threshold intensity value, which is set at a value smaller than the scan maximum intensity value associated with the uninterrupted parallel scanning beam.

In an embodiment, the intensity is analysed in the scan direction as a function of time from the initial scan edge to the final scan edge to determine the number of times the light intensity profile crosses the threshold intensity value. From the number of crossings of the threshold value in a scan, it is possible to determine the presence or absence of an intensity peak within the shadow region and, if an intensity peak is determined to be present, the presence or absence of a depressed region within the intensity peak.

Referring back to FIG. 6, a threshold intensity value 70 is set, for example it is stored in the processor analyzing the output signal from the photodetector. For example, the threshold value is of 50% of the maximum intensity 52 in the scan. The maximum scan intensity 52 can be determined by the processor as the intensity at the initial scan edge, i.e. initial scan time 56. Starting from the initial scan edge 56 to the final scan edge 56' in the scan direction, a first crossing of the intensity profile with the threshold line 70 is at time 53, which corresponds to the first shadow edge. A second crossing of the intensity profile is at time 57 (first peak edge), third crossing at time 58 (second peak edge), and a fourth crossing is at time 54 (second shadow edge). A number four of crossings is associated to the absence of defects in the inspected cross-sectional plane of the core rod.

In FIGS. 10 and 11, which represent the case of positive identification of at least a structural defect, the number of crossings of the intensity scan profile with the threshold line is six, namely, in the scan direction and starting from initial scan edge 84, at the first shadow edge 81, at the first peak edge 78, at the first and second edges 73 and 73' of the depressed region, at the second peak edge 79 and at the second shadow edge 81'. A number of crossings equal to two implies the absence of a central intensity peak and it is thus associated with the presence of a (large) defect or defects in the inspected cross-sectional plane of the core rod.

Preferably, the longitudinal extension of a defect is determined by inspecting the core rod at a plurality of positions along its longitudinal axis during stretching of the core rod, i.e. while the rod moves vertically relative to the inspection apparatus.

In another embodiment, determination of the longitudinal extension of a defect is carried out off-line.

In an embodiment, the processor processing the detected signals is configured to analyse the signals to check for the occurrence of a depression region in the central bright zone or for the absence of a central bright zone. If, as a result of analysing, a region of depressed intensity is determined to be present within the intensity peak or an intensity peak within the shadow region is determined to be absent, the processor is configured to identify the presence of at least one structural defect within the object's cross-section.

Preferably, the processor is configured to activate an alarm in case a structural defect is identified. In some preferred embodiments, identifying the presence of at least one structural defect comprises activating an alarm, wherein activating comprises recording a longitudinal position of the object's cross-section along the longitudinal axis at which the presence of at least one structural defect is identified as defective cross-section. The processor can be configured to record the longitudinal position in a memory within the processor or to transmit the longitudinal position of the defective cross-section to a computer (connected to the processor) that stores it.

Preferably, recording of the longitudinal position of the defect in the core rod makes possible, after completion of the stretching process, to select and discard longitudinal sections of the core rod containing defects.

Selection of longitudinal sections of the core rod can be performed automatically in known ways, such as by controlling the operation of a cutting tool customarily used at the end of the stretching process for cutting transversely the elongated glass core rod into a plurality of rod sections, also known as "canes" to be used for the manufacturing of a final glass preform for the production of an optical fibre. The cane is typically overclad by an overcladding layer, made by silica soot deposition to form a soot glass preform that undergoes consolidation to form a final glass preform to be drawn into an optical fibre.

In another embodiment, the alarm is an acoustic signal triggered by identification of a defect.

According to some embodiments, the processor is configured to analyse the intensity profile of each recorded scan to determine the number of crossings of the intensity profile with a predetermined threshold value and to activate an alarm in case the determined number of crossings is different from four, in practice if the number is two or six.

Although in the foregoing embodiments intensity profiles derive from analog electric signals (such as the recorded signal traces in an oscilloscope), it is to be understood that analysis can be performed on digital signals processed from analog signals, for example by associating a value 0 for the dark and a value 1 for light exceeding a given intensity threshold value. In an embodiment, an alarm is activated at the occurrence of 0 values within a time window corresponding to the central bright zone, i.e. the intensity peak, which may take place in the presence of a depressed region within the bright zone or in case of lack of detection of light in the shadow time region. The latter occurrence is generally indicative of the presence of large holes.

In the foregoing embodiments, defects can be detected if they are located in a cross-sectional area of the elongated object defined by the parallel rays impinging the object with d≤$d_{min}$ (e.g. area 62 of FIG. 8).

Figure 13:
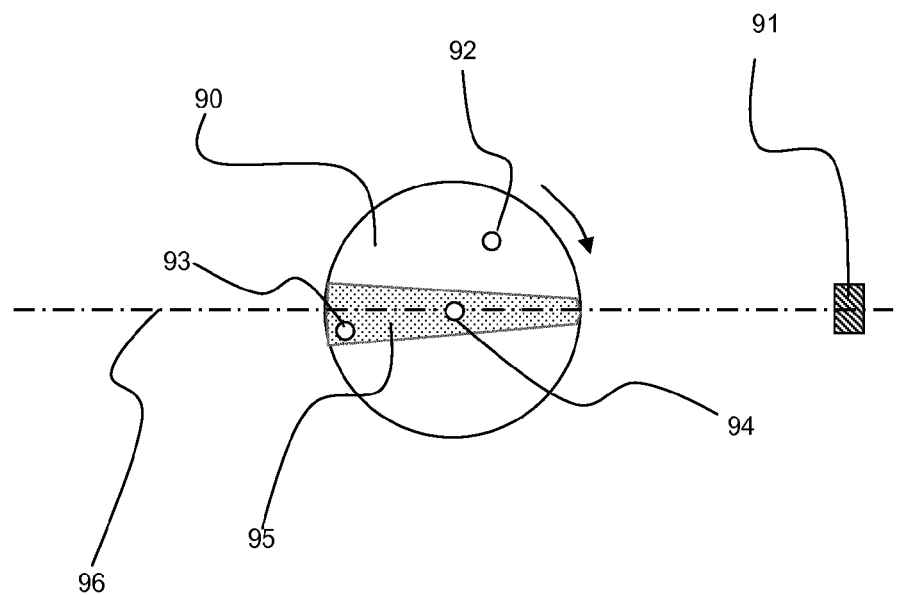
FIG. 13 is a schematic diagram showing a configuration of a receiving system with respect to a transparent object shown in a cross-sectional view including defects at various locations of the cross-section.

FIG. 13 is a schematic diagram showing a configuration of a receiving system with respect to a transparent object shown in a cross-sectional view including defects at various locations of the cross-section. In the figure, focussing lens system is omitted. In the example of FIG. 13, defects 93 and 94 are located within the cross-sectional area 95 of glass rod 90 where transmitted rays can be detected by photodetector 91, whereas defect 92 lies outside the detectable area 95.

In an embodiment, the glass rod is rotating about its own longitudinal axis during inspection and a plurality of scans, i.e. at least two, are recorded over a full rotation of the object. The rotation allows the investigation of defects, such as defect 92, temporarily outside the detectable cross-sectional area 95 in FIG. 13.

Preferably, the rotation of rod 90 is carried out at a constant speed. The rotation of the glass rod is preferably done on-line during stretching, for example by using the stretching apparatus described in US 2003/0140658, which allows the simultaneous traction and rotation of the rod. In this preferred embodiment, stretching process is carried out while imparting a rotation to the elongated object exiting the furnace, since it allows to search for and detect a defect at different angular positions of the core rod with respect to the incident beam. For example, rotation is uniform and of from 4 to 8 turns/minute. It is noted that time necessary for the acquisition of a scan by means of an inspection apparatus such as that described with reference to FIG. 3 is of about 0.5 ms and thus typical speed of rotation of the preform during elongation allow the recordal of a plurality of measurements in the same cross-sectional plane of the rod.

Advancement speed of the glass rod during the process of stretching a core preform is typically very small when compared with the acquisition time of an intensity scan so that a specific axial position of a void can be accurately determined. In an embodiment, the advancement speed is of from 15 to 25 cm/min.

When inspection for the presence of defects is performed off-line, rotation can be imparted to the rod by any known means during measurement.

Applicant noted that defects located in a peripheral cross-sectional area very near to the object surface are often associated with surface impurities that are generally removed in subsequent process steps of the manufacturing of the optical fibre preform, such as the fire-polishing of the core rod before the overclad deposition phase. Therefore, surface defects, including peripheral defects located close to the surface, will not generally affect the fibre quality. It is further noted that, in glass preforms obtained from common deposition and consolidation techniques, a great majority of the internal structural defects are positioned in a central cross-sectional area, since they originate from an incomplete or faulty closure of the axial hole of core preforms, for example in core glass preforms made by PCVD, MCVD or OVD.

The Applicant has realised that light spots, which are caused by surface impurities, can be discriminated from the light originating from the internal defects by a method that employs a double reading of the inspection plane along two orthogonal directions.

Figure 14:
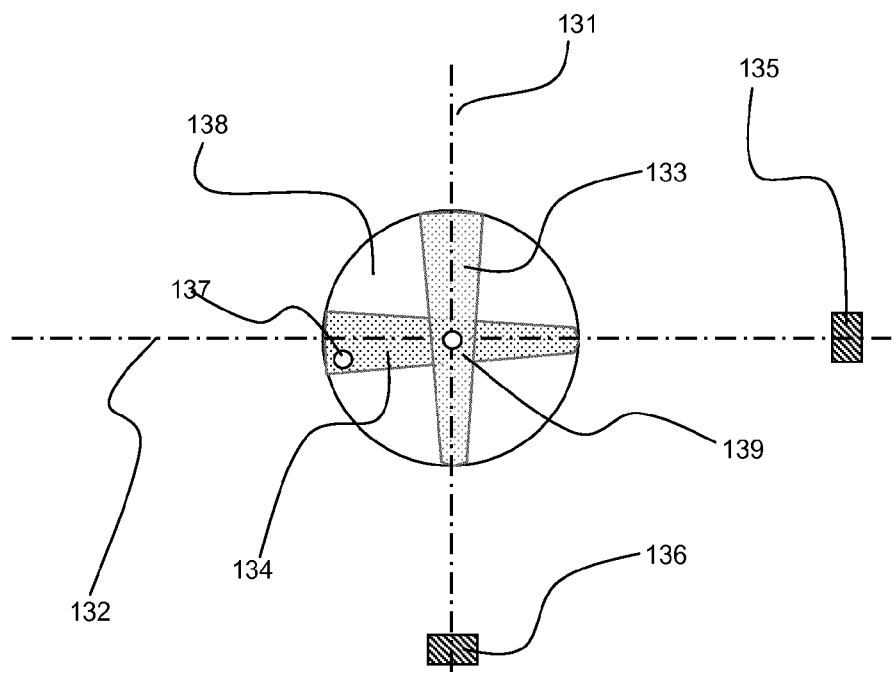
FIG. 14 is a schematic diagram showing a configuration of a receiving system, according to a further embodiment, with respect to a transparent object shown in a cross-sectional view including defects at different locations of the cross-section.

FIG. 14 shows diagrammatically the receiving system of an inspection apparatus in accordance with an embodiment. Glass rod 138, viewed in a cross-section, is scanned along the two axes, 131 and 132, which are perpendicular one another in a cross-sectional plane of the rod. The respective detectable areas of the glass rod for the first and second parallel scanning beam are indicated as dotted areas 133 and 134. Preferably, the scan axes are perpendicular to the longitudinal direction of the rod. Scanning beams along axes 131 and 132, which are transmitted through the glass rod, are collected by respective first and second photodetectors 136 and 135. A surface defect, such as 137, is detected only in one of the two detectable areas, namely area 134, by second photodetector 135. Conversely, a central defect, such as hole 139, is located in both detectable areas and therefore is detected by both photodetectors.

A comparison of the signals outputs from the first and second photodetectors, which are individually processed to convert the signals into a respective intensity scan profile, provides the information on the location of the detected defect, as a surface defect will be detected only by one of the two photodetectors, whereas a central defect will be shown in the central bright region of both scan profiles or, if of large size, as a missing bright region in both scan profiles. In this way, it possible to discriminate between central and peripheral defects, thereby minimizing errors that may lead to a higher waste volumes of discarded intermediate products.

Figure 15:
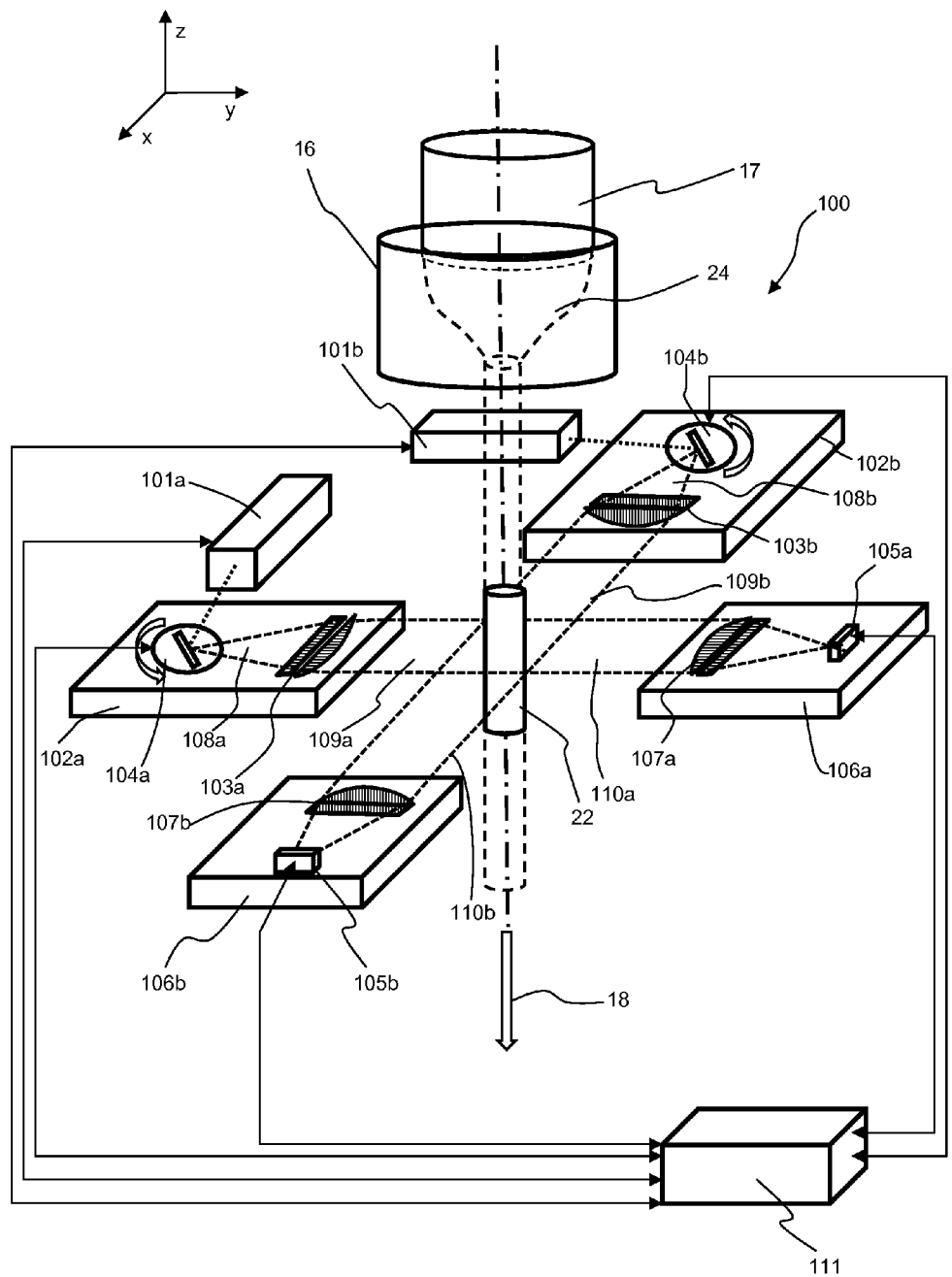
FIG. 15 is a schematic representation of an apparatus to implement a method in accordance with a further embodiment consistent with the present disclosure.

FIG. 15 is a diagrammatic perspective view of an inspection apparatus in combination with a stretching apparatus for the elongation of a glass core preform, in accordance with a further embodiment consistent with the present disclosure. Same reference numbers of FIG. 3 indicate same or like elements. In particular, a glass core preform 17 is fed vertically into a furnace 16. The melted portion from the neckdown region flows out the furnace 16 and cools while being stretched downwards (along the pulling direction indicated with arrow 18) so as to form an elongated glass preform 22 of specific diameter, i.e. the core rod.

An inspection apparatus 100 for inspecting the glass rod 22 comprises a first and second optical sources 101a and 101b configured to emit a respective first and second coherent optical beam, directed to a respective rotatable scanner 104a and 104b. Preferably, the first and second optical beams emitted by the optical sources are at a respective wavelength in the visible spectrum. More preferably, the emission wavelength of the first and second optical beams are the same. For example, both the first and second optical source is a HeNe laser device emitting a collimated beam in the visible spectrum at 630 nm.

First and second rotatable scanners receive the optical beam emitted from the respective optical source and are configured to produce a respective first and second scanning beams 108a and 108b. A first and second collimating optical system 103a and 103b are arranged to receive, respectively, the first and second optical scanning beam 108a and 108b and to convert them into a respective parallel scanning beam 109a and 109b, i.e. a scanning beam of parallel rays. The respective optical axis of the first and second collimating optical system is arranged in the plane of the scanning optical beam 108a and 108b. The rotatable scanners are arranged with respect to one another so that the first parallel scanning beam 109a is directed along a first incidence direction (y-axis) and it is swept in a first scan direction (along the x-axis)). The first incidence direction is orthogonal to a second incidence direction (x-axis) of the second parallel scanning beam 109b, which is swept in a second scan direction (along the y-axis) orthogonal to the first scan direction, the two scanning directions forming an inspection plane. The orthogonal scanning beams cross one another in an area of the inspection plane comprising a cross-sectional plane of the core rod.

Preferably, the inspection plane (i.e. the xy plane) is orthogonal to the longitudinal axis of the core rod (z-axis in FIG. 15), which corresponds, in the preferred embodiments, to the direction of advancement of the core rod.

In an embodiment, each of the collimating optical systems 103a and 103b comprises an optical edge sensor and one or more collimating lenses for converting the received optical beam into a beam of parallel rays. Preferably, each rotatable scanner is a rotatable mirror, which is configured to rotate at a constant angular rate dβ/dt across a scan angle β, sufficiently wide so that the area swept by the reflected beam is larger than the cross section of the elongated object to be measured in the inspection plane.

The first and second scanning beams 110a, 110b, which are transmitted through the core rod, are collected by a respective receiving system comprising a respective focussing optical system 107a, 107b, e.g. a collection lens, each being operably arranged so as to receive the transmitted scanned beam, i.e. the uninterrupted rays and the rays deflected by the rod, and a respective photodetector 105a, 105b, each being operably arranged to detect the beam collected by the focussing optical system.

The core rod 22 intercepts the first and second parallel scanning beams and the receiving systems are disposed at the opposite side of the core rod with respect to the respective optical sources, in position to receive the rays transmitted through the rod.

Components 103a and 104a for producing the first parallel scanning incident beam and the receiving system for collecting and detecting the scanned beam transmitted through the elongated object along the first scan direction (105a and 107a) can be placed on a respective bench plate 102a and 106a. Similarly, components 103b and 104b for producing the second parallel scanning incident beam and the receiving system for collecting and detecting the scanned beam transmitted through the elongated object along the second scan direction can be placed on a respective bench plate 102b and 106b.

First and second photodetectors 105a and 105b, preferably, comprise edge sensing preamplifier electronics for detecting the start and end of each sweep, and each of the photodetector is operably connected to a signal processor 111 configured to receive the output signals from the photodetectors. Preferably, the signal processor is configured to control the operation of laser devices 101a and 101b and of the rotatable scanners 104a and 104b (control and output lines indicated in the figure with double arrows).

The processor 111 is configured to receive a first electric signal output from first photodetector 105a and a second electric signal from second photodetector 105b, and to generate from the first and second electrical signals, respectively, a first light intensity profile in a first scan direction and a second light intensity profile in a second scan direction.

An example of a commercial apparatus with double-axis detection and suitable for carrying out the method consistent with the present disclosure is the Beta Laser-Mike Accuscan LD1025XY-S.

First and second intensity profiles are compared, e.g. by mathematical software components per se known and running in processor 111, to determine if one of the following conditions is satisfied:

(a) an intensity peak is absent in both scan profiles;

(b) an intensity peak comprising a region of depressed intensity is present in both scan profiles, and (c) a positive intensity peak is determined to be absent in one of first and second scan profiles and an intensity peak with a depressed region is determined to be present in the other of first and second scan profiles.

The presence of at least one structural defect in an inner region of the object's cross-section, i.e. a centrally located defect, is identified and then an alarm is activated if one of the conditions (a) to (c) is satisfied.

If a depressed region is present or the intensity peak is absent in only one of the two scan profiles (i.e. identification of a defect only in one scan direction), the processor does not proceed with the activation of the alarm.

If a depressed region is present in one of the two scan profiles and the intensity peak is absent in the other scan profile (i.e. identification of a defect in both scan directions, assumingly with different size in the two scan directions), the processor proceeds by activating the alarm.

Preferably, activating an alarm comprises recording (within the processor or in a computer connected to the processor) a longitudinal position of the object's cross-section along the longitudinal axis at which the presence of at least one centrally located structural defect is identified.

In some preferred embodiments, each intensity profile generated from the output of the respective photodetector is analysed in the respective scan direction as a function of time from the initial scan edge to the final scan edge to determine the number of times the intensity profile crosses a respective threshold intensity value, which may be set to be the same for both intensity profiles, relatively to the respectively scan maximum value. For example, the threshold intensity value if selected in the range of from 20% to 80% of the respective scan maximum value, preferably of from 30% to 70% of the scan maximum value.

The analysis outputs a first number of crossings for the first intensity profile and a second number of crossings for the second intensity profile. The first number of crossings of the threshold value is compared with the second number of crossings to determine if the first and second numbers of crossings are equal. In case first and second numbers are equal, two or six crossings indicate the presence of a centrally located structural defect whereas four crossings indicate the absence of defects. In case the first number is different from the second number, a number two or six in one intensity profile and a number four in the other intensity profile indicates the presence of a surface defect.

In many cases of interest, a centrally located defect is positioned within the core region of the core preform or in an annular region adjacent to the core region, which constitutes the inner cladding layer(s) of the optical fibre.

As possible outcome, a number two in one intensity profile and a number six in the other intensity profile indicates the presence of a very large inner defect (e.g. larger than 1 mm) mainly extending in one direction and thus lacking axial symmetry.

For example, comparison can be implemented by applying to the first and second intensity profiles a combination mathematical function that provides as result either 0 (i.e. no central defect) or 1 (i.e. central defect present). The result is 0 if one of the following conditions are satisfied: (i) first and second numbers are not equal one another and one of the two numbers is equal to four, or (ii) first and second numbers are equal one another and their value is four.

The result is 1 if one of the following conditions are satisfied: (iii) the first and second numbers are equal one another and their value is either two or six, and (iv) the first number of crossings is equal to two and the second number is equal to six. A result 1 identifies a centrally located defect by activating an alarm.

While in the preferred embodiments of FIGS. 3 and 14 a vertical elongation process is considered, in which the preform is elongated along a vertical axis, the method consistent with the general principles of the present disclosure can be applied in horizontal elongation processes, in which the preform is heated by means of an horizontally movable heater, e.g. a burner mounted on a carriage. An example of an horizontal elongation process is given in WO 2004/018373.

Although analysis of the structure is preferably performed on-line during stretching of a glass core preform, the method in accordance with the present disclosure can be carried out off-line. For example, a stretched core rod a final optical fibre preform can be inspected for the presence of defects, before severing the core rods into a plurality of core canes to be further processed for the production of an optical fibre preform to be drawn into an optical fibre.

The invention claimed is:

1. A method for inspecting defects inside a rod-shaped transparent object comprising:
   generating a first scanning beam of parallel light rays sweeping an inspection plane in a first scan direction;
   directing the first scanning beam onto a rod-shaped transparent object having a longitudinal axis and being arranged in such a way that the inspection plane is transverse to the longitudinal axis of the rod-shaped transparent object and comprises a cross-section of the rod-shaped transparent object;
   detecting the first scanning beam at an opposite side of the rod-shaped transparent object that is interposed to intercept the parallel light rays of the first scanning beam, thereby producing a first electric output signal, the first scanning beam producing a shadow of the rod-shaped transparent object;
   processing the first electric output signal to produce a first light intensity profile in the first scan direction, the first light intensity profile having a scan maximum value originating from the first scanning beam transmitted uninterrupted without interposition of the rod shaped transparent object and comprising a shadow region produced by a shadow of the rod-shaped transparent object, the shadow region being delimited by first and second shadow edges, the width between the first and second shadow edges being indicative of the outside diameter of the rod-shaped transparent object across the inspection plane;
   analyzing the first light intensity profile, wherein analyzing the first light intensity profile comprises
      setting a threshold intensity value smaller than the scan maximum value, and
      determining whether an intensity of the first intensity profile exceeds the threshold intensity value across the shadow region between the first and second shadow edges for checking presence or absence of an intensity peak within the shadow region; wherein:
   an intensity peak is determined to be absent when the intensity of the first intensity profile is determined to be smaller than the threshold intensity value across the shadow region;
   an intensity peak is determined to be present when a plurality of intensity values exceed the threshold intensity value across the shadow region, the intensity peak originating from detecting the deflected rays transmitted through the rod-shaped transparent object and
   the method further comprising identifying a presence of at least one structural defect within the rod-shaped transparent object's cross-section when a region of depressed intensity is determined to be present in the intensity peak, the depressed intensity region having a depth defined by a difference between a maximum intensity of the intensity peak and an intensity across the depressed intensity region, the intensity across the depressed intensity region being at least 20% smaller than the maximum intensity of the intensity peak, and analyzing the first light intensity profile further comprises determining if the intensity peak has a region of intensity values smaller than the threshold intensity value for checking the presence of a region of depressed intensity.

2. The method of claim 1, further comprising activating an alarm upon identifying the presence of the at least one structural defect.

3. The method of claim 2, wherein activating the alarm comprises:
   recording a longitudinal position of the rod-shaped transparent object's cross-section along the longitudinal axis at which the absence of the intensity peak or the presence of a region of depressed intensity is positively determined.

4. The method of claim 1, wherein the rod-shaped transparent object is a glass core rod for the production of an optical fibre.

5. The method of claim 1, wherein the depressed intensity region is delimited in the first scan direction by a first and second depression edges defining a width of the depressed region within the intensity peak, the method further comprising;
   determining the width of the depressed region,
   retrieving a correlation function defining a relationship between width values and diameter values of structural defects as a calibration curve, and
   calculating a diameter value of the at least one detected structural defect, the diameter value corresponding to the determined width of the depressed region by using the calibration curve.

6. The method of claim 1, wherein the threshold intensity value is from 20% to 80% of the scan maximum value.

7. The method of claim 1, wherein the rod-shaped transparent object is a glass core rod for the manufacturing of an optical fibre and the method is carried out in combination with a process for elongating a glass core preform comprising:
   providing a glass core preform;
   heating the glass core preform within a furnace so as to soften a lower portion thereof, and
   submitting the glass core preform to a traction which comprises pulling the softened lower end of the glass core preform out of the furnace along an advancement direction so as to form a glass core rod as a rod-shaped transparent object,
   wherein directing the first scanning beam is directing the first scanning beam onto the glass core rod, the inspection plane is positioned downstream the furnace along the advancement direction, and the glass core rod moves in the advancement direction, vertically relative to the inspection plane.

8. The method of claim 7, wherein submitting a traction is carried out while rotating the glass core rod about its longitudinal axis.

9. The method of claim 8, wherein detecting the first scanning beam is performed at a first angular position of the rotating glass core rod and the method further comprises repeating detecting the first scanning beam at a second angular position of the rotating glass core rod during a single rotation to produce an additional electric output signal, processing the additional electric output signal into an additional light intensity profile in the first scan direction, the additional light intensity profile having a scan maximum value originating from the first scanning beam transmitted at the second angular position uninterrupted without interposition of the rod shaped transparent object and comprising a shadow region produced by a shadow of the rod-shaped transparent object, the shadow region of the additional light intensity profile being delimited by first and second shadow edges of the additional light intensity profile, the width between the first and second edges of the additional light intensity profile being indicative of the outside diameter of the rod-shaped transparent object across the inspection plane; analyzing the additional light intensity profile, wherein analyzing the additional light intensity profile comprises setting a threshold intensity value of the additional light intensity profile smaller than the scan maximum value of the additional light intensity profile, and determining whether an intensity of the additional intensity profile exceeds the threshold intensity value of the additional light intensity profile across the shadow region between the first and second shadow edges of the additional light intensity profile for checking presence or absence of an intensity peak within the shadow region of the additional light intensity profile; wherein:

an intensity peak is determined to be absent when the intensity of the additional intensity profile is determined to be smaller than the threshold intensity value of the additional light intensity profile across the shadow region of the additional light intensity profile;

an intensity peak is determined to be present when a plurality of intensity values exceed the threshold intensity value of the additional light intensity profile across the shadow region of the additional light intensity profile, the intensity peak of the additional light intensity profile originating from detecting the deflected rays transmitted through the rod-shaped transparent object and the method further comprising identifying a presence of at least one structural defect within the rod-shaped transparent object's cross-section at the second angular position when a region of depressed intensity is determined to be present in the intensity peak of the additional light intensity profile, the depressed intensity region of the additional light intensity profile having a depth defined by a difference between a maximum intensity of the intensity peak of the additional light intensity profile and an intensity across the depressed intensity region of the additional light intensity profile, the intensity across the depressed intensity region of the additional light intensity profile being at least 20% smaller than the maximum intensity of the intensity peak of the additional light intensity profile, and analyzing the additional light intensity profile further comprises determining if the intensity peak of the additional light intensity profile has a region of intensity values smaller than the threshold intensity value of the additional light intensity profile for checking the presence of a region of depressed intensity.

10. A process for elongating a glass core preform for the production of an optical fibre, the process comprising:

providing a glass core preform;

heating a glass core preform within a furnace so as to soften a lower portion thereof, and submitting the glass core preform to a traction which comprises pulling the softened lower end of the glass core preform out of the furnace along an advancement direction so as to form an elongated glass core rod, and inspecting the glass core rod for defects in an inspection plane downstream the furnace, wherein inspecting is carried out according to the method of claim 1.

11. A method for inspecting defects inside a rod-shaped transparent object comprising:

generating a first scanning beam of parallel light rays sweeping an inspection plane in a first scan direction;

directing the first scanning beam onto a rod-shaped transparent object having a longitudinal axis and being arranged in such a way that the inspection plane is transverse to the longitudinal axis of the rod-shaped transparent object and comprises a cross-section of the rod-shaped transparent object;

detecting the first scanning beam at an opposite side of the rod-shaped transparent object that is interposed to intercept the parallel light rays of the first scanning beam, thereby producing a first electric output signal, the first scanning beam producing a shadow of the rod-shaped transparent object;

processing the first electric output signal to produce a first light intensity profile in the first scan direction, wherein the first light intensity profile ranges from an initial scan edge to a final scan edge in the first scan direction, the first light intensity profile having a scan maximum value originating from the first scanning beam transmitted uninterrupted without interposition of the rod shaped transparent object and comprising a shadow region produced by the shadow of the rod-shaped transparent object, the shadow region being delimited by first and second shadow edges, the width between the first and second shadow edges being indicative of the outside diameter of the rod-shaped transparent object across the inspection plane;

analyzing the first light intensity profile to determine a presence or absence of an intensity peak within the shadow region, the intensity peak originating from detecting the deflected rays transmitted through the rod-shaped transparent object, and identifying a presence of at least one structural defect within the rod-shaped transparent object's cross-section when a region of depressed intensity is determined to be present in the intensity peak, the depressed intensity region having a depth defined by a difference between the maximum intensity of the intensity peak and an intensity across the depressed intensity region, the intensity across the depressed intensity region being at least 20% smaller than the maximum intensity of the intensity peak, wherein analyzing the first light light-intensity profile comprises:

setting a threshold intensity value smaller than the scan maximum value;

determining the number of times the light intensity profile crosses the threshold intensity value in the first scan direction as a number of crossings to determine the presence or absence of an intensity peak or of a depressed region within the peak, wherein determining the presence or absence of an intensity peak or of a depressed region within the peak comprises:

determining that the intensity peak within the shadow region is absent when the number of crossings is two in the first scan direction, determining that the intensity peak is present and further determining that a depressed region within the intensity peak is absent when the number of crossings is four in the first scan direction, and determining that an intensity peak and a depressed region within the intensity peak are present when the number of crossings is six in the first scan direction.

\* \* \* \* \*